United States Patent [19] | [11] 4,172,044
Zeidler et al. | [45] Oct. 23, 1979

[54] PROCESS AND CONCENTRATES FOR CLEAR-RINSING IN MECHANICAL DISHWASHING

[75] Inventors: Ulrich Zeidler; Albertus van Wageningen, both of Düsseldorf; Dieter Grodau, Hilden; Eric Sung, Monheim; Theodor Altenschöpfer, Düsseldorf, all of Fed. Rep. of Germany

[73] Assignee: Henkel Kommanditgesellschaft auf Aktien (Hunkel KGaA), Dusseldorf-Holthausen, Fed. Rep. of Germany

[21] Appl. No.: 837,691

[22] Filed: Sep. 29, 1977

[30] Foreign Application Priority Data

Oct. 1, 1976 [DE] Fed. Rep. of Germany ....... 2644542

[51] Int. Cl.[2] ...................... B01D 19/02; C07C 69/16; C07C 69/28; C11D 1/722

[52] U.S. Cl. ...................................... 252/142; 252/99; 252/143; 252/170; 252/173; 252/321; 252/358; 252/174.21; 252/DIG. 1; 252/DIG. 14; 134/26; 560/263

[58] Field of Search ................... 252/89, 99, 135, 142, 252/143, 170, 173, 321, 358, DIG. 14; 134/26; 560/263

[56] References Cited

U.S. PATENT DOCUMENTS

| | | | |
|---|---|---|---|
| 3,758,410 | 9/1973 | Liu | 252/89 |
| 3,775,330 | 11/1973 | Batka | 252/89 |
| 3,779,934 | 12/1973 | Altenschopfer | 252/142 |
| 3,969,134 | 7/1976 | Batka | 252/351 X |
| 3,993,605 | 11/1976 | Scholz-Weigl | 252/358 X |
| 4,088,598 | 5/1978 | Williams | 252/135 |

FOREIGN PATENT DOCUMENTS 1910765 10/1969 Fed. Rep. of Germany ........... 252/551

*Primary Examiner*—Dennis L. Albrecht
*Attorney, Agent, or Firm*—Hammond & Littell

[57] ABSTRACT

Process for the rinsing of dishes in dishwashing machines having one or several clear-rinsing cycles using an aqueous solution of an adduct of from 2 to 14 moles of ethylene oxide and from 0 to 7 mols of propylene oxide to the monocarboxylic acid ester of an alkanediol with a linear alkane chain of 8 to 20 carbon atoms, and having vicinal hydroxyls, as well as clear-rinsing concentrates for use in the process.

20 Claims, No Drawings

PROCESS AND CONCENTRATES FOR CLEAR-RINSING IN MECHANICAL DISHWASHING

BACKGROUND OF THE INVENTION

In mechanical dishwashing generally two cleaning cycles, usually separated by intermediate rinsing cycles with pure water are used. In the two cleaning cycles, different products are utilized. In the first or true cleaning cycle, alkaline-reacting agents are employed for the loosening and emulsifying of the food residues. In the after-rinsing or clear-rinsing bath, on the other hand, special clear-rinsing agents are employed. The latter should possess a good wetting power and be able to reduce the surface tension of the after-rinsing water to such a degree that it drains in a film-like manner from the dishes and leaves no visible deposits, such as lime spots or other impurities.

Because of the violent agitation of the liquor in the dishwasher, these clear-rinsing agents have to be as low-foaming as possible. The customary anionic wetting agents, however, such as higher-molecular-weight alkyl sulfates or alkyl sulfonates or aralkyl sulfonates are not generally usable because they foam too much. In practice, therefore, mostly nonionic tensides based on ethylene-oxide adducts to fatty alcohols, alkylphenols, or polypropylene glycols of higher molecular weights are employed. These products, however, were also found in actual practice to be not sufficiently low-foaming in the concentration range, required for a sufficient wetting effect.

These adducts have been found to cause disturbances due to excessive foam formation particularly in commercial dishwashing machines which have a very high rate of water circulation and a very high return rate of the clear-rinsing liquor into the main rinsing cycle. The same difficulties may also arise in home dishwashing machines. Even with the use of relatively low-foaming ethylene-oxide adducts, it is therefore necessary to add anti-foaming agents to the clear-rinsing agents. Suitable nonionic alkoxylation products are those which are slightly soluble at rinsing temperatures, such as ethylene-oxide adducts to higher alcohols or alkyl phenols with a low degree of ethoxylation or suitable adducts of ethylene oxide and propylene oxide. Such products possess, however, no wetting effect at the application temperatures and thus present a burden for the clear-rinsing agent.

In addition to this, the applied wetting agents should possess a good biological degradability and a low toxicity toward the organisms living in water. These features were not previously found to be available along with a good wetting and draining effect.

In U.S. Pat. No. 3,775,330, a low-foaming clear-rinsing composition adapted for mechanical dishwashers was disclosed, consisting essentially of (A) an adduct of from 5 to 20 mols of ethylene oxide and from 1 to 10 mols of propylene oxide to an alkanediol having a linear alkane chain with from 10 to 20 carbon atoms and vicinal, non-terminal hydroxyls, and (B) a lower organic carboxylic acid having from 2 to 6 carbon atoms and sequestering properties toward salts causing water hardness, wherein the weight ratio between component (A) and component (B) is from 1:0.2 to 1.3; together with the process for the mechanical washing of dishes comprising subjecting dirty dishes to the action of a washing solution, subjecting the washed dishes to at least one clear-rinising solution and recovering said washed dishes, the improvement consisting of utilizing an aqueous solution containing from 0.01 to 1.0 gm. per liter of an adduct of from 5 to 20 mols of ethylene oxide and from 1 to 10 mols of propylene oxide to an alkanediol having a linear alkane chain with from 10 to 20 carbon atoms and vicinal, non-terminal hydroxyls, as said at least one clear-rinsing solution.

In U.S. Pat. No. 3,779,934, a clear-rinsing composition of an aqueous solution of an adduct of from 3 to 30 mols of ethylene oxide to alkanediols with a linear alkane chain of from 10 to 20 carbon atoms and having vicinal non-terminal hydroxyls, was disclosed and employed.

In U.S. Pat. No. 3,969,134, a clear-rinsing composition of an aqueous solution of (a) from 50% to 100% by weight of an adduct of from 5 to 20 mols of ethylene oxide and from 1 to 10 mols of propylene oxide to a secondary alkanol having a linear alkane chain of from 10 to 20 carbon atoms and (b) from 0 to 50% by weight of an adduct of from 5 to 10 mols of ethylene oxide to a secondary alkanol having a chain length of from 11 to 15 carbon atoms was disclosed and employed.

OBJECTS OF THE INVENTION

An object of the invention is the development of lowfoaming and biologically-degradable clear-rinsing agents for mechanical dishwashing with a good wetting and draining effect toward hard surfaces.

Another object of the invention is the development in the process for the mechanical washing of dishes which comprises subjecting dirty dishes to the action of a washing solution, subjecting the washed dishes to at least one clear-rinsing solution and recovering said washed dishes, the improvement consisting of utilizing an aqueous solution containing from 0.01 to 0.5 grams per liter of at least one alkoxylated hydroxyalkyl ester of the formula

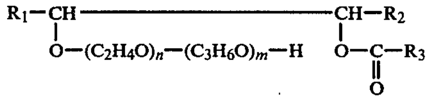

wherein $R_1$ and $R_2$ are members selected from the group consisting of (a) similar and different alkyl having from 1 to 17 carbon atoms where the sum of the carbon atoms in $R_1$ and $R_2$ is from 6 to 18 and (b) one hydrogen and one alkyl having from 8 to 14 carbon atoms, $R_3$ is a member selected from the group consisting of alkyl having from 1 to 12 carbon atoms and a hydrocarbon aryl having from 6 to 12 carbon atoms, n is an integer from 2 to 14, m is an integer from 1 to 7 when both $R_1$ and $R_2$ are alkyl and an integer from 0 to 7 when one of $R_1$ or $R_2$ is hydrogen, as said at least one clear-rinsing solution.

A further object of the present invention is the development of a low-foaming concentrate adapted for use in the clear-rinse cycle of dishwashers consisting essentially of (A) from 25% to 75% by weight of water and (B) from 25% to 75% by weight of a clear-rinsing agent consisting essentially of (a) from 50% to 100% by weight of at least one alkoxylated hydroxyalkyl ester of the formula

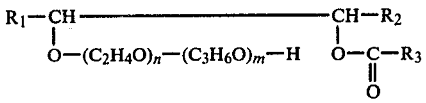

wherein $R_1$ and $R_2$ are members selected from the group consisting of (a') similar and different alkyl having from 1 to 17 carbon atoms where the sum of the carbon atoms in $R_1$ and $R_2$ is from 6 to 18 and (b') one hydrogen and one alkyl having from 8 to 14 carbon atoms, $R_3$ is a member selected from the group consisting of alkyl having from 1 to 12 carbon atoms and a hydrocarbon aryl having from 6 to 12 carbon atoms, n is an integer from 2 to 14, m is an integer from 1 to 7, and (b) from 0 to 50% by weight of at least one alkoxylated hydroxyalkyl ester of the formula

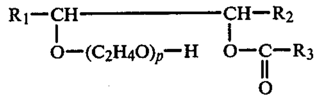

wherein $R_1$, $R_2$, and $R_3$ have the above assigned values and p is an integer from 5 to 14, wherein said clear-rinsing agent further contains (1) from 0 to 40% by weight, based on the weight of said clear-rinsing agent of a water-soluble lower organic hydroxycarboxylic acid having from 2 to 6 carbon atoms and sequestering properties toward salts causing water hardness and (2) from 0 to 40% by weight, based on the weight of said clear-rinsing agent of a water-miscible lower alcohol.

These and other objects of the invention will become more apparent as the description thereof proceeds.

DESCRIPTION OF THE INVENTION

The purpose of the invention was the production of an extremely low-foaming and biodegradable clear rinse agent which obviates the additional use of foam depressing tensides or other foam depressants. This purpose is achieved according to the invention by a clear rinse compound for machine dishwashing based on nonionic low-foaming tensides with a content of alkylene oxide adducts on hydroxyl group containing compounds, characterized by the fact that they contain as alkylene oxide adducts on hydroxyl group containing compounds at least one alkoxylated hydroxyalkyl ester of the formula (I)

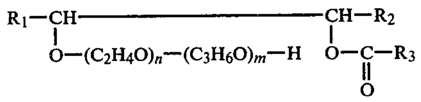
(I)

in which the symbols $R_1$, $R_2$, $R_3$, n, and m have the following meaning:

$R_1$ and $R_2$ are hydrogen or similar or different alkyls with 1 to 17 carbon atoms each with the spcification that $R_1$ and $R_2$ together have 6 to 18, preferably 8 to 16, carbon atoms when they both stand for an alkyl and that if one of the radicals $R_1$ and $R_2$ stands for hydrogen, the other radical represents an alkyl radical with 8 to 14, preferably 10 to 12 carbon atoms; $R_3$ is an alkyl radical with 1 to 12, preferably 1 to 3 carbon atoms or an aryl radical, especially the phenyl radical; n is a whole number from 2 to 14, preferably from 5 to 10; m is a whole number from 1 to 7, when $R_1$ and $R_2$ stand for an alkyl radical; or m is a whole number from 0 to 7, preferably from 0 to 5, and especially from 1 to 4, when one of the radicals $R_1$ and $R_2$ represents hydrogen.

More particularly, the present invention relates to the improvement in the process for the mechanical washing of dishes which comprises subjecting dirty dishes to the action of a washing solution, subjecting the washed dishes to at least one clear-rinsing solution and recovering said washed dishes, the improvement consists of utilizing an aqueous solution containing from 0.01 to 0.5, preferably from 0.03 to 3, grams per liter of at least one alkoxylated hydroxyalkyl ester of the formula

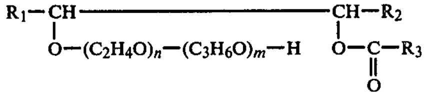

wherein $R_1$ and $R_2$ are members selected from the group consisting of (a) alkyl having from 1 to 17 carbon atoms where the sum of the carbon atoms in $R_1$ and $R_2$ is from 6 to 18, preferably from 8 to 16 and (b) one hydrogen and one alkyl having from 8 to 14, preferably from 10 to 12 carbon atoms, $R_3$ is a member selected from the group consisting of alkyl having from 1 to 12, preferably 1 to 3, carbon atoms and a hydrocarbon aryl having from 6 to 12 carbon atoms, preferably phenyl; n is an integer from 2 to 14, preferably from 5 to 10, m is an integer from 1 to 7 when both $R_1$ and $R_2$ are alkyl and an integer from 0 to 7, preferably from 0 to 5, and especially from 1 to 4, when one of $R_1$ or $R_2$ is hydrogen, as said at least one clear-rinsing solution.

The invention also relates to a low-foaming concentrate adapted for use in the clear-rinse cylce of dishwashers consisting essentially of (A) from 25% to 75%, preferably from 30% to 60%, by weight of water and (B) from 25% to 75%, preferably 40% to 70%, by weight of a clear-rinsing agent consisting essentially of (a) from 50% to 100% by weight of at least one alkoxylated hydroxyalkyl ester of the formula

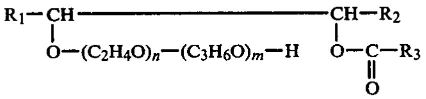

wherein $R_1$ and $R_2$ are members selected from the group consisting of (a) alkyl having from 1 to 17 carbon atoms where the sum of the carbon atoms in $R_1$ and $R_2$ is from 6 to 18 and (b') one hydrogen and one alkyl having from 8 to 14 carbon atoms, $R_3$ is a member selected from the group consisting of alkyl having from 1 to 12 carbon atoms and a hydrocarbon aryl having from 6 to 12 carbon atoms, n is an integer from 2 to 14, m is an integer from 1 to 7, and (b) from 0 to 50% by weight of at least one alkoxylated hydroxyalkyl ester of the formula

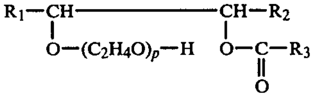

wherein $R_1$, $R_2$, and $R_3$ have the above assigned values and p is an integer from 5 to 14, wherein said clear-rinsing agent further contains (1) from 0 to 40%, preferably from 5% to 35%, by weight, based on the weight of said clear-rinsing agent of a water-soluble lower organic carboxylic acid having from 2 to 6 carbon atoms and sequestering properties toward salts causing water hardness and (2) from 0 to 40% by weight, based on the weight of said clear-rinsing agent of a water-miscible lower alcohol. The said concentrate can also contain from 0 to 1%, preferably from 0.05% to 1%, of at least one preservative.

The clear rinse agents according to the invention possess the desired advantageous properties to a high degree. Especially, they are extremely low foaming and/or practically foamless. They are very water-soluble even at the rinse temperatures (50° to 70° C.) and show a distinct wetting activity with regard to the goods being rinsed.

The cloud points, determined according to DIN 53917, lie below 70° C., preferably between 10° and 40° C., and especially between 15° and 35° C.

The adducts of Formula I used according to the invention may, for example, be obtained in a two-step synthesis by the reaction of epoxy alkanes of the Formula II

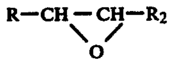

II with a carboxylic acid of the Formula III $R_3—COOH$ III in the presence of a weakly alkaline catalyst to obtain a compound of the Formula IV

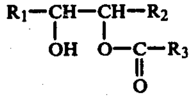

IV which is then alkoxylated in the also known way (preferably with an acidic catalyst) with n mols of ethylene oxide and then with m mols of propylene oxide. Preferably on alkoxylation, the amount of ethylene oxide is greater than the amount of propylene oxide and usually at least twice as great on a molar basis. The preferred ratio of ethylene oxide units to propylene oxide units is 1:0.2 to 0.6. However, the alkoxylated hydorxyalkyl esters may also be prepared by other known processes.

The symbols $R_1$, $R_2$, $R_3$, n, and m in the Formulas II to IV have the same meanings indicated for Formula I. Epoxy alkanes with a terminal epoxy group are especially suitable for this process.

The epoxyalkanes (II) used as starting materials which have a nonterminal or terminal epoxy group are obtained from the corresponding olefins and/or olefin mixtures by basically known methods.

A variety of commercially available mixtures of monoolefins are available as starting materials for the preparation of the above-mentioned epoxyalkanes.

Suitable mixtures of monoolefins can be obtained by dehydrogenation (catalytically or by chlorination followed by dehydrochlorination) of linear paraffins of 11 to 20 carbon atoms followed by removal of the monoolefin content of the reaction product (by distillation or selective extraction, as may be preferred). In the monoolefins the double bonds are substantially non-terminal and are distributed statistically along the "backbone"

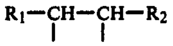

chain. Various fractions are obtainable from these monoolefin mixtures. Some of these monoolefins have the following chain length distributions:

(a) $C_{11}$–$C_{14}$ olefins:
- $C_{11}$ olefins, approximately 22 percent by weight,
- $C_{12}$ olefins, approximately 30 percent by weight,
- $C_{13}$ olefins, approximately 26 percent by weight,
- $C_{14}$ olefins, approximately 22 percent by weight, (b) $C_{15}$–$C_{18}$ olefins:
- $C_{15}$ olefins, approximately 26 percent by weight,
- $C_{16}$ olefins, approximately 35 percent by weight,
- $C_{17}$ olefins, approximately 32 percent by weight,
- $C_{18}$ olefins, approximately 7 percent by weight.

On the other hand, it is also possible to use olefin mixtures which are prepared by aluminochemical methods and which have unbranched alkyl chains with 12 or 20 carbon atoms. These mixtures have a high (i.e., more than 50%) proportion of terminal unsaturation. Examples of suitable commercial products are those having the chain length distributions shown below:

Olefin Fractions Used

| Fraction | % by Weight |
|---|---|
| (c) $C_{12}$–$C_{14}$ fraction | |
| $C_{12}$ Terminal | 55 |
| $C_{14}$ Terminal | 31 |
| $C_{12}$ Non-Term. | 5 |
| $C_{14}$ Non-Term. | 8 |
| (d) $C_{14}$–$C_{16}$ fraction | |
| $C_{14}$ Terminal | 53 |
| $C_{16}$ Terminal | 28 |
| $C_{14}$ Non-Term. | 7 |
| $C_{16}$ Non-Term. | 11 |
| (e) $C_{16}$–$C_{18}$ fraction | |
| $C_{16}$ Terminal | 35 |
| $C_{18}$ Terminal | 23 |
| $C_{20}$ Terminal | 2 |
| $C_{16}$ Non-Term. | 11 |
| $C_{18}$ Non-Term. | 21 |
| $C_{20}$ Non-Term. | 5 |

It is also possible to use olefin mixtures which contain saturated hydrocarbons when they are obtained with the olefin mixtures.

Terminal epoxyalkanes with chain lengths in the range of $C_{12}$–$C_{14}$ (c above) are preferred for the preparation of hydroxyalkyl esters of Formula I. Preferred nonterminal epoxy alkanes of Formula II are based on monoolefins of a $C_{11}$–$C_{14}$ fraction or a $C_{15}$–$C_{18}$ fraction (a and b above).

The required ethylene oxide-propylene oxide adducts may, if this should be desirable on account of cost, be combined with such adducts which contain exclusively ethylene oxide adducted on the above-mentioned hydroxyalkyl esters. Considered for this purpose should be especially the adducts of 5 to 10 mols of ethylene oxide on hydroxyalkyl esters of a chain length of $C_{12}$ to $C_{14}$. Such combinations, however, have an increased tendency to foam formation, which is why generally not more than 50% by weight of the ethylene oxide-propylene-oxide adducts should be replaced by the above-mentioned ethylene oxide adducts.

When used with the common goods to be rinsed like china plates, cutlery pieces and especially glasses which are considered especially difficult in this respect, the adducts show an excellent runoff and clear drying effect. They are, therefore, excellently suited for the clear rinsing of dishes after a preliminary cleaning cycle, for instance, with alkaline cleaners. Already at concentrations of about 0.01 grams per liter, a drop-free, filmlike runoff of the clear rinse solutions from the dishes takes place. In addition, the adducts are biodegradable corresponding to the EG guide lines.

The products or combinations are used in the clear-rinsing bath in concentrations of about 0.01 to 0.5 gm/l, preferably 0.03 to 0.3 gm/l of active substance. The application concentration depends to a certain degree on the kind of surface to be cleaned. It is hardly influenced by the water hardness. Especially plastic surfaces demand a somewhat higher amount of clear rinse agents. The application is effected preferably in the form of aqueous or aqueous-alcoholic concentrates with contents of 5% to 75%, preferably 10% to 60% by weight of the active components. Considered as alcoholic solvent components are preferably the water-miscible lower alcohols such as ethanol, propanol and isopropanol, ethylene glycol, propylene glycol, dipropylene glycol, the monoethyl ether of ethylene glycol, and similar compounds.

As far as the adducts themselves are liquids, they may also be applied in solvent-free form. The concentrates are suitably added with the help of automatic dosing devices of the type already common for similar purposes, or they may be added by hand to the clear rinse liquid.

Naturally, the clear rinse compounds may also contain other ingredients common to such materials. For instance, lower organic hydroxycarboxylic acids with 2 to 6 carbon atoms may be added to the concentrates and/or the clear rinse liquid for the prevention, among other things, of lime incrustations or lime haze on the rinsed dishes. Preferred are such acids which are physiologically harmless and which have complexing properties with the hardness forming cations in the water, for instance, tartaric acid, lactic acid, glycolic acid, and especially citric acid. The acid addition to the clear rinse concentrate is about 5% to 40% preferably 10% to 35% by weight. Acidically adjusted rinse compounds according to the invention are especially suited for use with household dishwashing machines because of their excellent runoff effect. In addition, the clear rinse agents according to the invention may contain minor amounts, mostly about 0.05 to 1.0% by weight, of preservatives like sodium benzoate or formaldehyde; as well as minor amounts, on the same basis of perfume oils.

The following specific embodiments are examples of the practice of the invention. They are not to be deemed limitative in any respect.

EXAMPLES

The alkoxylated hydroxyalkyl esters of Formula I, as employed according to the invention, can be prepared by the following method. A number of these alkoxylated hydroxyalkyl esters of Formula I are listed in Table 1 together with their cloud points.

(A) Production and Properties of Alkoxylated Hydroxyalkyl Esters 1 mol of an epoxyalkane of the Formula II was heated to 100° C. to 150° C. for about 2 to 7 hours with one mol of the carboxylic acid of Formula III in the presence of a weakly alkaline catalyst, such as an alkali metal acetate, a tertiary amine and/or a tertiary phosphine, or a quaternary ammonium compound, which catalyst should be present in amounts of 0.1 to 3 mol %. Subsequently, any possibly unreacted carboxylic acid is removed by extracting with water or vacuum distillation. The hydroxyalkyl ester of Formula IV so obtained is then reacted by known methods with the desired amount of ethylene oxide and then with the desired amount of propylene oxide. The alkoxylated hydroxyalkyl esters obtained are liquids, the cloud points of which in water are determined according to DIN method 53917. These values are reported in Table 1.

Table 1

| No. | Alkoxylated Hydroxyalkyl Ester Tenside | Cloud Point According to DIN 53917 °C. |
|---|---|---|
| 1 | 2-hydroxy-$C_{12/14}$-alkylacetate + 5EO/1PrO | 16 |
| 2 | 2-hydroxy-$C_{12/14}$-alkylacetate + 5EO/3PrO | 17 |
| 3 | 2-hydroxy-$C_{12/14}$-alkylacetate + 6EO/2PrO | 23 |
| 4 | 2-hydroxy-$C_{12/14}$-alkylacetate + 7EO | 30 |
| 5 | 2-hydroxy-$C_{12/14}$-alkylacetate + 7EO/1PrO | 29 |
| 6 | 2-hydroxy-$C_{12/14}$-alkylacetate + 7EO/2PrO | 24 |
| 7 | 2-hydroxy-$C_{12/14}$-alkylacetate + 8EO/3PrO | 33 |
| 8 | 2-hydroxy-$C_{16/18}$-alkylacetate + 5EO/1PrO | — |

The abbreviations used in the tables are
EO = ethylene oxide
PrO = propylene oxide (B) Foam Properties The foam behavior of different clear rinses and/or clear rinse mixtures according to the invention were tested in a foam plunger test (hand plunger method according to DIN method 53902). The results of the test shown in Tables 2A and 2B demonstrate the extremely favorable foam behavior of the tested compounds.

At a dosage of 0.2 gm of the compound in question (Table 2A), or mixture (Table 2B) per liter of water, the aqueous solutions of the compounds or mixtures indicated in the Tables were maintained at a temperature of 50° C. in a measuring cylinder and were stamped 20 times and thereupon the foam height in cm was determined after 10, 30 and 60 seconds. The city water used had a hardness of 16° dH (German degrees of hardness).

Table 2A

| Compound No. | Dosage = 0.2 gm of the Compound In 1 liter of City Water, 50° C. | Foam Height in cm After 10 sec | 30 sec | 60 sec |
|---|---|---|---|---|
| 1 | 2-hydroxy-$C_{12/14}$-alkylacetate + 5EO/1PrO | 1.0 | 1.0 | 1.0 |
| 2 | 2-hydroxy-$C_{12/14}$-alkylacetate + 5EO/3PrO | 1.0 | 0.7 | 0.5 |
| 3 | 2-hydroxy-$C_{12/14}$-alkylacetate + 6EO/2PrO | 0.9 | 0.9 | 0.7 |
| 4 | 2-hydroxy-$C_{12/14}$-alkylacetate + 7EO | 4.0 | 3.0 | 2.5 |
| 5 | 2-hydroxy-$C_{12/14}$-alkylacetate + 7EO/1PrO | 2.5 | 1.5 | 1.5 |
| 6 | 2-hydroxy-$C_{12/14}$-alkylacetate + 7EO/2PrO | 2.0 | 1.5 | 1.5 |
| 7 | 2-hydroxy-$C_{12/14}$-alkylacetate + 8EO/3PrO | 2.0 | 2.0 | 1.5 |

Table 2B

| Dosage = 0.2 gm of the Mixture in 1 liter of City Water, 50° C. | Foam Height in cm After 10 sec | 30 sec | 60 sec |
|---|---|---|---|
| 50% 2-hydroxy-$C_{12/14}$-alkylacetate + 7EO + 50% 2-hydroxy-$C_{12/14}$-alkylacetate + 5EO/3PrO | 2.0 | 1.5 | 1.0 |
| 25% 2-hydroxy-$C_{12/14}$-alkylacetate + 7EO + 75% 2-hydroxy-$C_{12/14}$-alkylacetate + 5EO/3PrO | 1.0 | 1.0 | 1.0 |

Table 2B-continued

| Dosage = 0.2 gm of the Mixture in 1 liter of City Water, 50° C. | Foam Height in cm After 10 sec | 30 sec | 60 sec |
|---|---|---|---|
| 50% 2-hydroxy-$C_{12/14}$-alkylacetate + 7EO + 50% 2-hydroxy-$C_{12/14}$-alkylacetate + 6EO/2PrO | 2.5 | 2.0 | 2.0 |
| 25% 2-hydroxy-$C_{12/14}$-alkylacetate + 7EO + 75% 2-hydroxy-$C_{12/14}$-alkylacetate + 6EO/2PrO | 3.0 | 2.0 | 1.5 |
| 75% 2-hydroxy-$C_{12/14}$-alkylacetate + 7EO/2PrO + 25% citric acid | 1.5 | 1.0 | 1.0 |
| 67% 2-hydroxy-$C_{12/14}$-alkylacetate + 5EO/3PrO + 33% citric acid | 1.0 | 1.0 | 0.5 |
| 50% 2-hydroxy-$C_{12/14}$-alkylacetate + 6EO/2PrO + 50% citric acid | 1.0 | 1.0 | 0.5 |
| 15% 2-hydroxy-$C_{12/14}$-alkylacetate + 7EO + 45% 2-hydroxy-$C_{12/14}$-alkylacetate + 5EO/3PrO + 40% citric acid | 1.3 | 1.0 | 0.7 |
| 20% 2-hydroxy-$C_{12/14}$-alkylacetate + 7EO + 60% 2-hydroxy-$C_{12/14}$-alkylacetate + 6EO/2PrO + 20% citric acid | 1.5 | 1.2 | 1.0 |

(C) Biodegradability

The biodegradability of the alkoxylated hydroxyalkyl esters was determined in the OECD screening test according to the EG guidelines and reported as % BiAS (Bismuth Active Substance) decrease. According to this, the tested compounds are BiAS active and have a Marlophene® equivalency of 61% to 62%, that is, an active substance content of 100% of the compounds are equivalent to 61% or 62%, respectively, BiAS. Marlophene® is a polyglycol ether of an alkylphenol nonionic tenside. The degradation test in the screening test gave in both cases high BiAS decrease of >90% after 12 or 19 days, respectively, as shown in Table 3. Thus, the tested compounds correspond fully to the EG guide lines.

Table 3

| Compound | AS Content in % | BiAS Content in % | Ratio AS/BiAS≙% Marlophene® Equivalency | % BiAS Decrease After Days 12 | 19 |
|---|---|---|---|---|---|
| 2-hydroxy-$C_{12/14}$-alkylacetate + 7EO | 100 | 62.4 | 62 | 98 | 98 |
| 2-hydroxy-$C_{12/14}$-alkylacetate + 7EO/2PrO | 100 | 61.0 | 61 | 99 | 97 |

EXAMPLE 1

A very effective clear rinse agent for dishwashing machines had the following composition in percent by weight:

20% 2-hydroxy-$C_{12/14}$-alkylacetate+7EO/2PrO
28% isopropanol
52% water

The agent remained clear and stable in storage between −1° C. and +70° C. No annoying foam appeared at the use temperature of 50° C. The clear drying effect is good across a range of concentration from 0.3 to 0.9 gm/l in the clear rinse liquid.

EXAMPLE 2

An acid clear rinse agent especially suited for application in household dishwashing machines had the following composition in percent by weight:

20% 2-hydroxy-$C_{12/14}$-alkylacetate+7EO/2PrO
20% citric acid
18% isopropanol
42% water This agent also remained clear and stable in storage between −1° C. and +70° C. The foam appearing at the use temperature of 50° C. was practically negligible. The clear drying effect in hard as well as in soft water across a range of concentration from 0.2 to 0.9 gm/l in the clear rinse liquid was very good.

EXAMPLE 3

A clear rinse agent according to the invention for dishwashing machines, especially for household dishwashing machines, had the following composition in percent by weight:

17.5% 2-hydroxy-$C_{16/18}$-alkylacetate+5EO/1PrO
19.5% citric acid
19.0% isopropanol
0.3% sodium benzoate
0.2% formaldehyde solution (35%)
43.5% completely demineralized water The clear drying effect is good across a range of concentration from 0.1 to 1.0 gm/l. Foam development cannot be observed at a liquid temperature of at least 50° C.

Example 4

A result comparable to that obtained with the formulation in Example 3 was obtained with the following formulation:

17.5% 2-hydroxy-$C_{12/14}$-alkylacetate+7EO/2PrO
19.5% citric acid
19.0% isopropanol
0.3% sodium benzoate
0.2% formaldehyde solution (35%)
43.5% completely demineralized water

EXAMPLES 5 TO 14

Clear rinse agents of the following composition, according to the invention, were prepared by use of completely demineralized water where the tensile numbers correspond to those of Table 1, and where the amounts are given in percent by weight:

Table 4

| Tenside No. | Tenside % | Citric Acid % | Isopropanol % | Na Benzoate % | Formaldehyde Solution (35%) % | Water % |
|---|---|---|---|---|---|---|
| 1 | 20.0 | — | 32.0 | 0.3 | 0.2 | 47.5 |
| 2 | 20.0 | — | 33.0 | 0.3 | 0.2 | 46.5 |
| 3 | 20.0 | — | 30.0 | 0.3 | 0.2 | 49.5 |
| 5 | 20.0 | — | 28.0 | 0.3 | 0.2 | 51.5 |
| 7 | 20.0 | — | 27.5 | 0.3 | 0.2 | 52.0 |
| 1 | 20.0 | 20.0 | 19.0 | 0.3 | 0.2 | 40.5 |
| 2 | 20.0 | 20.0 | 21.0 | 0.3 | 0.2 | 38.5 |
| 3 | 20.0 | 20.0 | 21.0 | 0.3 | 0.2 | 38.5 |
| 5 | 20.0 | 20.0 | 18.0 | 0.3 | 0.2 | 41.5 |
| 7 | 20.0 | 20.0 | 18.0 | 0.3 | 0.2 | 41.5 |

The cloud points of the clear rinse agents in Table 4 lie below 20° C. The clear rinse agents were clear and stable in storage at temperatures between −1° C. and +70° C. All compounds were extremely low foaming to foamless at 50° C. liquid temperatures. The neutral clear rinse agents showed, at a concentration of 0.3 gm/l of the clear rinse liquid, excellent clear drying effects. Their effectiveness was still somewhat exceeded by the acid clear rinse agents.

EXAMPLES 15 AND 16

Two further clear rinse agents according to the invention had the following composition in percent by weight:

(15)

22.5% 2-hydroxy-$C_{12/14}$-alkylacetate+5EO/3PrO
7.5% 2-hydroxy-$C_{12/14}$-alkylacetate+7EO
17.0% dipropylene glycol
15.0% isopropanol
0.3% sodium benzoate
0.2% formaldehyde solution (35%)
37.5% completely demineralized water (16)

12.0% 2-hydroxy-$C_{12/14}$-alkylacetate+6EO/2PrO
4.0% 2-hydroxy-$C_{12/14}$-alkylacetate+7EO
23.3% citric acid
20.0% isopropanol
0.3% sodium benzoate
0.2% formaldehyde solution (35%)
0.7% perfume oil
39.5% completely demineralized water The clear drying effect of these agents was very good across a range of concentration of from 0.2 to 0.7 gm/l. The foam formation was extremely low.

The preceding specific embodiments are illustrative of the practice of the invention. It is to be understood, however, that other expedients known to those skilled in the art, or disclosed herein, may be employed without departing from the spirit of the invention or the scope of the appended claims.

We claim:

1. The process for the mechanical washing of dishes which comprises subjecting dirty dishes to the action of a washing solution, subjecting the washed dishes to at least one clear-rinsing solution and recovering said washed dishes, the improvement consisting of utilizing an aqueous solution containing from 0.01 to 0.5 grams per liter of at least one alkoxylated hydroxyalkyl ester of the formula

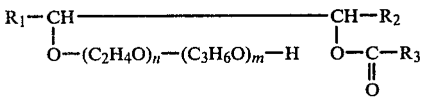

wherein $R_1$ and $R_2$ are members selected from the group consisting of (a) similar and different alkyl having from 1 to 17 carbon atoms where the sum of the carbon atoms in $R_1$ and $R_2$ is from 6 to 18 and (b) one hydrogen and one alkyl having from 8 to 14 carbon atoms, $R_3$ is a member selected from the group consisting of alkyl having from 1 to 12 carbon atoms and a hydrocarbon aryl having from 6 to 12 carbon atoms, n is an integer from 2 to 14, m is an integer from 1 to 7 when both $R_1$ and $R_2$ are alkyl and an integer from 0 to 7 when one of $R_1$ or $R_2$ is hydrogen, as said at least one clear-rinsing solution.

2. The process of claim 1 wherein one of $R_1$ and $R_2$ is hydrogen and the other is alkyl having 8 to 14 carbon atoms.

3. The process of claim 1 wherein one of $R_1$ and $R_2$ is hydrogen and the other is alkyl having 10 to 12 carbon atoms.

4. The process of claim 1 wherein one of $R_1$ and $R_2$ is hydrogen, the other is alkyl having 10 to 12 carbon atoms and the ratio of n to m is 1:0.2 to 0.6.

5. The process of claim 1 wherein n is from 5 to 10 and m is from 1 to 4.

6. The process of claim 1 wherein said alkoxylated hydroxyalkyl ester is the adduct of 7 mols of ethylene oxide and 2 mols of propylene oxide onto 1 mol of 2-hydroxy-$C_{12/14}$-alkylacetate.

7. The process of claim 1 wherein said alkoxylated hydroxyalkyl ester is a mixture from 50% to 90% by weight of a compound where one of $R_1$ and $R_2$ is hydrogen and the other is alkyl having 10 to 12 carbon atoms, n is an integer from 5 to 10 and m is an integer from 1 to 4 and from 10% to 50% by weight of a compound where one of $R_1$ and $R_2$ is hydrogen and the other is alkyl having 10 to 12 carbon atoms, n is an integer from 5 to 10 and m is 0.

8. The process of claim 7 wherein said mixture is a mixture of 50% to 90% by weight of an adduct of 5 mols of ethylene oxide and 3 mols of propylene oxide onto 1 mol of 2-hydroxy-$C_{12/14}$-alkylacetate and 10% to 50% by weight of an adduct of 7 mols of ethylene oxide onto 1 mol of 2-hydroxy-$C_{12/14}$-alkylacetate.

9. A low-foaming concentrate adapted for use in the clear-rinse cycle of dishwashers consisting essentially of (A) from 25% to 75% by weight of water and (B) from 25% to 75% by weight of a clear-rinsing agent consisting essentially of (a) from 50% to 100% by weight of at least one alkoxylated hydroxyalkyl ester of the formula

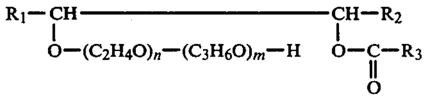

wherein $R_1$ and $R_2$ are members selected from the group consisting of (a') similar and different alkyl having from 1 to 17 carbon atoms where the sum of the carbon atoms in $R_1$ and $R_2$ is from 6 to 18 and (b') one hydrogen and one alkyl having from 8 to 14 carbon atoms, $R_3$ is a member selected from the group consisting of alkyl having from 1 to 12 carbon atoms and a hydrocarbon aryl having from 6 to 12 carbon atoms, n is an integer from 2 to 14, m is an integer from 1 to 7 when both $R_1$ and $R_2$ are alkyl and an integer from 0 to 7 when one of $R_1$ and $R_2$ is hydrogen, and (b) from 0 to 50% by weight of at least one alkoxylated hydroxyalkyl ester of the formula

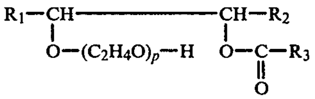

wherein $R_1$, $R_2$, and $R_3$ have the above assigned values and p is an integer from 5 to 14, wherein said clear-rinsing agent further contains (1) from 0 to 40% by weight, based on the weight of said clear-rinsing agent of a water-soluble lower organic hydroxycarboxylic acid having from 2 to 6 carbon atoms and sequestering properties toward salts causing water hardness and (2) from 0 to 40% by weight, based on the weight of said clear-rinsing agent of a water-miscible lower alcohol.

10. The low-foaming concentrate of claim 9 wherein one of $R_1$ and $R_2$ is hydrogen and the other is alkyl having 8 to 14 carbon atoms.

11. The low-foaming concentrate of claim 9 wherein one of $R_1$ and $R_2$ is hydrogen and the other is alkyl having 10 to 12 carbon atoms.

12. The low-foaming concentrate of claim 9 wherein one of $R_1$ and $R_2$ is hydrogen, the other is alkyl having 10 to 12 carbon atoms and the ratio of n to m is 1:0.2 to 0.6.

13. The low-foaming concentrate of claim 9 wherein n is from 5 to 10 and m is from 1 to 4.

14. The low-foaming concentrate of claim 9 wherein said alkoxylated hydroxyalkyl ester is the adduct of 7 mols of ethylene oxide and 2 mols of propylene oxide onto 1 mol of 2-hydroxy-$C_{12/14}$-alkylacetate.

15. The low-foaming concentrate of claim 9 wherein said alkoxylated hydroxyalkyl ester is a mixture from 50% to 90% by weight of a compound where one of $R_1$ and $R_2$ is hydrogen and the other is alkyl having 10 to 12 carbon atoms, n is an integer from 5 to 10 and m is an integer from 1 to 4 and from 10% to 50% by weight of a compound where one of $R_1$ and $R_2$ is hydrogen and the other is alkyl having 10 to 12 carbon atoms, n is an integer from 5 to 10 and m is 0.

16. The low-foaming concentrate of claim 15 wherein said mixture is a mixture of 50% to 90% by weight of an adduct of 5 mols of ethylene oxide and 3 mols of propylene oxide onto 1 mol of 2-hydroxy-$C_{12/14}$-alkylacetate and 10% to 50% by weight of an adduct of 7 mols of ethylene oxide onto 1 mol of 2-hydroxy-$C_{12/14}$-alkylacetate.

17. The low-foaming concentrate of claim 9 wherein said clear-rinsing agent further contains from 5% to 40% by weight of said water-soluble lower organic hydroxycarboxylic acid.

18. The low-foaming concentrate of claim 9 wherein said clear-rinsing agent further contains from 10% to 35% by weight of said water-soluble lower organic hydroxycarboxylic acid.

19. The low-foaming concentrate of claim 18 wherein said water-soluble lower organic hydroxycarboxylic acid is citric acid.

20. The low-foaming concentrate of claim 9 wherein said clear-rinsing agent has a further content of from 0.05% to 1% based on the weight of said clear-rinsing agent of a preservative.

* * * * *

UNITED STATES PATENT AND TRADEMARK OFFICE

CERTIFICATE OF CORRECTION

PATENT NO. : 4,172,044

DATED : October 23, 1979

INVENTOR(S) : ULRICH ZEIDLER et al.

It is certified that error appears in the above-identified patent and that said Letters Patent are hereby corrected as shown below:

Column 5, line 47, "hydorxyalkyl" should read --hydroxyalkyl--.

Column 6, line 21, "12 or" should read -- 12 to --.

Column 10, line 41, "tensile" should read -- tenside --.

Signed and Sealed this

*First* Day of *April 1980*

[SEAL]

*Attest:*

SIDNEY A. DIAMOND

*Attesting Officer* *Commissioner of Patents and Trademarks*